United States Patent [19]

Zimmermann

[11] Patent Number: 4,837,372

[45] Date of Patent: Jun. 6, 1989

[54] PROCESS FOR OLIGOMERIZATION OF OLEFINS

[75] Inventor: Heinz Zimmermann, Munich, Fed. Rep. of Germany

[73] Assignee: Linde Aktiengesellschaft, Wiesbaden, Fed. Rep. of Germany

[21] Appl. No.: 78,508

[22] Filed: Jul. 28, 1987

[30] Foreign Application Priority Data

Jul. 29, 1986 [DE] Fed. Rep. of Germany ....... 3625572
Jul. 29, 1986 [DE] Fed. Rep. of Germany ....... 3625571

[51] Int. Cl.$^4$ ............................ C07C 2/08; C07C 2/14
[52] U.S. Cl. ..................................... 585/514; 585/520; 502/224; 502/231
[58] Field of Search ................ 585/514, 520; 502/224, 502/231

[56] References Cited

U.S. PATENT DOCUMENTS 2,734,047 2/1956 Smith ................................... 502/224
3,678,120 7/1972 Bloch ................................... 502/224
3,925,194 12/1975 Rodewald ........................... 502/224
3,925,251 12/1975 Rodewald ........................... 502/224
4,465,893 8/1984 Ohah ................................... 502/224

FOREIGN PATENT DOCUMENTS 0188830 7/1986 European Pat. Off. .
0068554 1/1983 European Pat. Off. .

Primary Examiner—Asok Pal
Attorney, Agent, or Firm—Millen & White

[57] ABSTRACT

Oligomerization and isomerization of olefins, e.g., butene, is performed in the gas phase on a solid catalyst containing a superacid fluorine compound of an element of Group III, IV and/or V of the periodic table, e.g. $Al_2O_3$ impregnated with a superacid or a salt thereof. e.g. $HBF_4$, $(NH_4)_2SiF_6$, $H_2SiF_6$, $NH_4BF_4$ or $HPF_6$. The process is particularly applicable for increasing the olefin yield in steam cracking plants or for the recovery of fuel components from FCC residual gases.

12 Claims, No Drawings

PROCESS FOR OLIGOMERIZATION OF OLEFINS

BACKGROUND OF THE INVENTION

This invention relates to a process for the oligomerization of olefins.

In many fields of polymerization processing, in order to obtain the desired properties and production throughput, it is conventional to stop the polymerization at a low degree of polymerization. Such industrial oligomerization process require the establishment of satisfactory systems for providing the olefins as well as for the oligomerization itself.

In the case of olefin recovery in steam cracking plants, the yields of the individual olefins are present on the basis of the thermodynamics or the reaction kinetics. A substantial increase in the yield of a specific olefin, while employing constant cracking conditions can be achieved only by recycling the products. But in the case of thermal cracking of feedstocks containing hydrocarbons, besides ethylene and propylene, other olefins are produced such as butenes, which cannot be recycled, since they would lead to a rapid coking of the cracking tubes in the steam cracking plant, which would in turn result in a loss of hydrocarbons.

Another application of olefin oligomerization reactions relates to the use of residual gases from fluidized catalytic cracking (FCC) processes. FCC residual gases are conventionally converted to fuel components in costly processes by alkylation or oligomerization liquid phase reactions. With the introduction of lead-free gasoline, such products have become of increasing importance as blend components. The liquefied FCC residual gases are released from the light components under pressure in a fractionating tower and are then reacted in the presence of a catalyst such as sulfuric acid, phosphoric acid or hydrogen fluoride. The reaction products are fractionated in a fractionating tower into a polymer or alkylate as bottoms product and light components as overhead product. The bottoms product is fractionated throughout the boiling range, with the residual gases being recycled to the process. This process is described in greater detail in "Hydrocarbon Processing", Vol. 60, No. 9, September 1981, pp. 134–138.

Disadvantages of the processes known so far are that the acids catalysts employed must be separated thereby requiring expensive processes in part caused by substantial environmental and corrosion problems. When dissolved catalysts (homogeneous catalysts) are used, the dissolved catalysts must also be separated from the product.

SUMMARY

An object of the invention is to provide an improved process for the oligomerization of olefins, and in particular to a process which avoids at least some of the disadvantages of the prior art.

Upon further study of the specification and appended claims, further objects and advantages of this invention will become apparent to those skilled in the art.

According to the invention these objects are obtained by conducting the oligomerization in the gas phase in contact with a catalytic quantity of a solid catalyst which contains a catalytic quantity of at leat one superacidic fluorine compound of an element of Groups III, IV and/or V of the periodic table.

Advantageously, a catalyst is used which comprises or consists essentially of an $Al_2O_3$ support with 0.1 to 30% by weight, preferably 5 to 15% by weight, or superacidic fluorine compounds, based on the weight of the total of the alumina and superacidic fluorine compounds.

As superacidic fluorine compounds, all acids are suitable which contain elements of Group III, IV and/or V of the periodic table. Examples of such superacids include, but are not limited to, $HBF_4$, $H_2SiF_6$ and $HPF_6$. Salts of superacids such as, for example, $NH_4BF_4$ or $(NH_4)_2SiF_6$ can also be used with equally good results. It is within the scope of the invention that acids or salts other than those mentioned can be used.

In the context of this invention, superacids are intended to define those acids that are more strongly acidic than 100% sulfuric acid. Superacids generally have a pH of about $-0.5$ measured at 20° C.

The salts of the superacids which can be employed in the invention include but are not limited to ammonium salts, alkali metal salts, e.g., sodium; alkaline earth metal salts, e.g., calcium; heavy metal salts, e.g., iron, cobalt, etc., etc., with the provision that the cationic portion of the salt does not deleteriously interfere with the catalytic activity.

The catalyst used according to the invention for oligomerization is produced conventionally by impregnating the support with the superacid or with aqueous solutions of its salts and subsequent calcining, in which the superacid component is chemically bonded to the support.

The only support that has proven to be feasible for the purposes of the present invention is alumina.

Because of the fixed nature of the superacid, the reaction media are not corrosive, which together with the mild reaction conditions lead to favorable investment and operating costs.

The choice of superacid fluorine compounds of elements of Group III, IV and/or V of the periodic table has proved to be particularly favorable since with such superacidic catalysts, excellent yields with high selectivity under mild reaction conditions are obtained in the oligomerization of olefins.

Preferred conditions for the oligomerization are such that the reaction is conducted at a pressure of 1–80 bars, more preferably 5–50 bars, at a temperature of 100°–40° C., more preferably 100°–300° C., and at a weight hourly space velocity (WHSV) of 0.1–5 g/g h.

The process according to the invention enables the desired oligomerization of olefins, especially butenes, to be performed in an exceptionally advantageous way. This has particular application for example, to the recovery of olefins by thermal cracking from feedstocks containing hydrocarbons, wherein in order to increase the olefin yield, butene oligomers are partly recycled to the cracking step. Likewise, the oligomerization process of this invention can be used for the recovery of fuel components by oligomerization of FCC residual gases.

Studies of steam cracking plants for the production of ethylene and propylene have shown that by oligomerization or polymerization, especially di-, tri- and tetramerization, the butenes occurring in the cracking step can be converted into recyclable products which do not adversely affect the steam cracking plant. By oligomerization and recycling of the butenes, the olefin yield, i.e., the yield of ethylene and propylene, is increased by a total of about 2% by weight.

About 5 to 6% by weight of butenes based on the total reaction product are produced under conventional cracking conditions in the cracking of naphtha or gas oil. According to this invention, the butenes can be dimerized to about a 90% yield by superacid catalysts. Based on an average ethylene yield of 25% from the dimer/trimer gasoline so produced, this means an increase in the total ethylene yield from the butenes of $5 \times 0.9 \times 0.25 = 1.125\%$ by weight to $6 \times 0.9 \times 0.25 = 1.35\%$ by weight and a corresponding increase in propylene, assuming a propylene/ethylene ratio of 0.6, of about 0.8% by weight.

Besides oligomerization of butenes, the catalyst according to the invention also causes the isomerization of n-butenes to i-butene. This isomerization leads to a highly branched oligomers of high antiknock quality. The isomerization of 1- to 2-butene or of 2- to 1-butene takes place at temperatures above 150° C., while that of n- to i-butene requires temperatures above 300° C.

According to a suitable embodiment, butadiene is extracted before oligomerization from the stream containing butene. This butadiene separation step can be conducted in any conventional manner, e.g., extractive distillation, as described in "Industrial Organic Chemistry", published by Verlag Chemie, Weinheim, 1978, p. 96. This step is advisable, because butadiene tends to polymerize, thus yielding undesirable by-products.

Utilizing the process according to the invention, an increase in the yield in ethylene and propylene in steam cracking plants can be attained without changes or redesigning of the cracking furnace.

Moreover the $C_4$ butene dimers or trimers can alternatively be used as high-octane fuel components.

As mentioned above, olefins contained in FCC residual gases can also be oligomerized by the process of the invention. In this way, FCC residual gases can be processed into high-octane components.

$C_4$ FCC residual gases comprise for the most part, about 70% of olefins (10 to 15% by weight of i-butene with the remainder of the olefin being butene-1, cis- and trans-butene-2) and n- and i-butane. The butenes are oligomerized by the process according to the invention, during which a simultaneous isomerization of n-butene to i-butene occurs, thereby resulting in higher octane numbers.

In test engines, the oligomer gasolines were shown to exhibit an MON (Motor Octane Number) up to 85 an RON (Research Octane Number) up to 100. The oligomer gasolines, in a mixture with lead-free regular gasoline, showed blend octane numbers up to 89 MON and 108 RON.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following example(s), all temperatures are set forth uncorrected in degrees Celsius; unless otherwise indicated, all parts and percentages are by weight.

EXAMPLE 1

A butadiene-free $C_4$ cut from a steam cracking plant (raffinate 1) is conducted at 300° C. and 5 bars at a WHSV of 0.66 g/g.h over 150 ml of a superacidic catalyst, comprising an $Al_2O_3$ support containing 10% by weight of $HBF_4$. The oligomerization of the butenes takes place in contact with the catalyst under these mild reaction conditions. The product is condensed in a cold trap and analyzed.

From the analysis of the condensate and of the condenser residual gas, a conversion of 90.5%, in relation to butenes, is calculated. In particular, the oligomerization product amounts to 71.0% by weight of dimers and 28.5% by weight of trimers. In addition, traces of tetramers are detectable.

The product can be recycled for thermal cracking, as a result of which the yield of ethylene and propylene is increased.

EXAMPLE 2

A technical FCC $C_4$ cut (16% by weight of butene-1, 10% by weight of i-butene, 33% by weight of cis/trans-butene-2, 33% by weight of i/n-butane) is reacted at 10 bars, 250° C. and a WHSV of 0.66 g/g.h. The products are expanded and separated into gas and liquid products in a separator. From the analysis and the flow of gas and liquid phase, a conversion of 64% by weight is calculated, in relation to olefins contained in the feedstock. The catalyst employed was 10% by weight of $H_2SiF_6$ on alumina.

The product fraction 90°–200° C. (dimers and trimers) shown in the test engine a blend octane number for lead-free regular gasoline of 104 RON and 86.6 MON.

Other olefins aside from butenes can be oligomerized by this invention, such olefins preferably containing 2–30 carbon atoms. Examples of such olefins include, but are not limited to pentenes, hexenes, heptenes, octenes et cetera.

The preceding example(s) can be repeated with similar success by substituting the generically or specifically described reactants and/or operating conditions of this invention for those used in the preceding example(s).

With respect to all patent documents and literature references mentioned above, they are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

I claim:

1. A process for the oligomerization of olefins comprising oligomerizing at least one olefin in the gas phase in contact with an oligomerizing quantity of a solid catalyst containing a catalytic quantity of at least one superacidic fluorine compound said compound being $HBF_4$, $NH_4BF_4$, $H_2SiF_6$, $(NH_4)_2SiF_6$ or $HPF_6$.

2. A process according to claim 1, wherein the catalyst comprises an $Al_2O_3$ support containing 0.1–30% by weight of said at least one superacidic fluorine compound.

3. A process according to claim 1, wherein the catalyst comprises an $Al_2O_3$ support containing 5–15% by weight, of said at least one superacidic fluorine compound.

4. A process according to claim 1, wherein the oligomerization is performed at a pressure of 1–80 bars, at a temperature of 100°–400° C. and at a weight hourly space velocity of 0.1–5 g/g.h.

5. A process according to claim 1, wherein the oligomerization is performed at a pressure of 5–50 bars, at a temperature of 100°–300° C. and at a weight hourly space velocity of 0.1–5 g/g.h.

6. A process according to claim 1, wherein the oligomerization is conducted with an FCC residual gas containing said at least one olefin.

7. A process according to claim 1, wherein said at least one olefin is a butene.

8. A process according to claim 7, wherein said butene is 1-butene or iso-butene.

9. A process according to claim 2, wherein the oligomerization is conducted with an FCC residual flue gas containing said at least one olefin.

10. A process according to claim 2, wherein said at least one olefin is a butene.

11. A process according to claim 10, wherein the oligomerization is performed at a pressure of 1–80 bars, at a temperature of 100°–400° C. and at a weight hourly space velocity of 0.1–5 g/g.h.

12. A process according to claim 10, wherein the oligomerization is performed at a pressure of 5–50 bars, at a temperature of 100°–300° C. at a weight hourly space velocity of 0.1–5 g/g.h.

* * * * *